US008299416B2

(12) United States Patent
Arbore et al.

(10) Patent No.: US 8,299,416 B2
(45) Date of Patent: Oct. 30, 2012

(54) HIGH SPEED QUANTUM EFFICIENCY MEASUREMENT APPARATUS UTILIZING SOLID STATE LIGHTSOURCE

(75) Inventors: Mark A. Arbore, Los Altos, CA (US); David L Klein, Palo Alto, CA (US); Leonid A. Vasilyev, Beaverton, OR (US); John M. Schmidt, Oakland, CA (US); James E. Hudson, Portland, OR (US); Gregory S. Horner, Felton, CA (US)

(73) Assignee: Tau Science Corporation, Felton, CA (US)

( * ) Notice: Subject to any disclaimer, the term of this patent is extended or adjusted under 35 U.S.C. 154(b) by 428 days.

(21) Appl. No.: 12/660,688

(22) Filed: Mar. 1, 2010

(65) Prior Publication Data
US 2010/0219327 A1 Sep. 2, 2010

Related U.S. Application Data

(60) Provisional application No. 61/156,532, filed on Mar. 1, 2009.

(51) Int. Cl.
*G01N 21/64* (2006.01)
*G01J 1/58* (2006.01)
(52) U.S. Cl. ............. 250/222.2; 250/459.1; 702/182
(58) Field of Classification Search ......... 250/222.2, 250/206, 458.1, 459.1; 702/182; 382/167; 356/445–448
See application file for complete search history.

(56) References Cited

U.S. PATENT DOCUMENTS

| 5,376,810 A | * | 12/1994 | Hoenk et al. ........... 257/228 |
| 6,171,885 B1 | * | 1/2001 | Fan et al. ................ 438/70 |
| 6,597,398 B1 | * | 7/2003 | Booth, Jr. .............. 348/272 |

OTHER PUBLICATIONS

Fischer et al. (2002) Scanning IQE-Measurement for Accurate Current Determination on Very Large Area Solar Cells. 29th IEEE Photovoltaic Specialists Conference, May 20-24, 2002 New Orleans, Louisiana, pp. 454-457.

* cited by examiner

*Primary Examiner* — Seung C Sohn
(74) *Attorney, Agent, or Firm* — Lumen Patent Firm

(57) ABSTRACT

The present invention provides a high-speed Quantum Efficiency (QE) measurement device that includes at least one device under test (DUT), at least one conditioned light source with a less than 50 nm bandwidth, where a portion of the conditioned light source is monitored. Delivery optics are provided to direct the conditioned light to the DUT, a controller drives the conditioned light source in a time dependent operation, and at least one reflectance measurement assembly receives a portion of the conditioned light reflected from the DUT. A time-resolved measurement device includes a current measurement device and/or a voltage measurement device disposed to resolve a current and/or voltage generated in the DUT by each conditioned light source, where a sufficiently programmed computer determines and outputs a QE value for each DUT according to an incident intensity of at least one wavelength of from the conditioned light source and the time-resolved measurement.

18 Claims, 9 Drawing Sheets

600

*(a)*

*(b)*

700

(a)

(b)

800

(a)

(b)

(c)

1000

(a)

(b)

(c)

HIGH SPEED QUANTUM EFFICIENCY MEASUREMENT APPARATUS UTILIZING SOLID STATE LIGHTSOURCE

CROSS-REFERENCE TO RELATED APPLICATIONS

This application is cross-referenced to and claims the benefit from U.S. Provisional Application 61/156,532 filed Mar. 1, 2009, and which are hereby incorporated by reference.

FIELD OF THE INVENTION

The invention relates to measurement of the conversion of light energy to electrical energy. More specifically, the invention relates to a high-speed time-resolved quantum efficiency measurement device from a conditioned light source.

BACKGROUND

Photodiodes and solar cells are often characterized by quantum efficiency (QE) and responsivity to measure the optical-to-electrical conversion efficiency of the device. Quantum Efficiency is expressed in units of outgoing electrons per incident photon, while Responsivity is expressed in units of outgoing current per incident Watt (A/W). Further, spectral response (SR) is a measure of the device conversion efficiency as a function of incident photon wavelength or optical frequency. Spectral response can be expressed as either QE or responsivity with respect to wavelength by a simple conversion of units.

Historically, apparatuses used to measure QE have used a conventional broadband lightsource such as Quartz Tungsten Halogen, Xenon Arc, or Metal Halide, where the light is spectrally resolved with either a wavelength scanning monochromator or a set of bandpass filters. For example, FIG. 1 shows a conventional QE measurement system 100 that includes a lamp 102, a monochromator 104, an order sorting filter 107, an optical chopper 108, a lens system 110, a quasi-monochromatic light 112, a device under test (DUT) 114, and a current monitor 116 (typically a lock-in amplifier or other synchronous detection circuit).

QE measurements are made sequentially as the apparatus is mechanically stepped through a series of predetermined wavelengths by adjusting either the monochromator 104 diffraction grating 106 angle or placing individual bandpass filters into the beam of broadband light. The resultant light 112 (often called monochromatic, but typically exhibiting a bandwidth in the range of 5-20 nm) is directed at the DUT 114, and the current output of the DUT 114 is recorded and normalized to the incident light 112 intensity.

Monochromator-based systems as described in FIG. 1 offer adjustable wavelength resolution and essentially continuous coverage over the range of interest. For solar cells, the range of interest can include wavelengths from the shortest solar emissions around 300 nm to the wavelength corresponding to the smallest bandgap present in the active region of the device, for example approximately 1100 nm for Silicon, and longer for some other materials. However, when scanning such a large wavelength range, monochromators require the use of order-sorting filters to prevent higher order diffraction ($\lambda/2$, $\lambda/3$ . . . ) from reaching the output slit, and also leak a measurable amount of broadband stray light that can not readily be removed by filters.

Interference filter-based systems offer good stray light rejection, but use multi-layer dielectric films that eventually degrade due to direct exposure to the high intensity, and UV-containing, broadband lightsource. Filters must be regularly checked and replaced to preserve data integrity. Filter designs with wide rejection bands (required for use with a broadband light source) tend to be both inefficient (with peak transmission <50%) and expensive. Such filters tend not to be tunable (via tilting the angle of incidence with respect to the filter) over a wide wavelength range: typical tuning ranges are ~5% of the nominal wavelength. Traditional filter designs with wide rejection bands suffer significant increase in losses as they are tuned via tilting.

Both monochromators and interference filters require a collimated incident beam in order to function optimally, with an increasingly tight collimation requirement as the passband width is decreased. Because conventional sources emit light with a poor etendue, a significant throughput penalty must be suffered when integrating such sources with a monochromator. This throughput penalty is in addition to the inherent losses associated with selecting a small portion of the lamp spectrum, and with the internal inefficiencies of the monochromator itself. Hence, conventional sources cannot deliver spectrally selected light efficiently to a QE measuring system. This is the origin of the very high power consumption that is common to existing systems. Additionally, the unstable light output (both short term and long term) of conventional light sources necessitates frequent calibrations and bulb replacement.

In both monochromator and interference filter systems, a basic limitation is the speed with which the system can scan through a set of wavelengths. Mechanical motion must occur to step from one wavelength to the next, and this limits the practical throughput of the system. Due to the small fraction of total light striking the sample at any time, scans may take ~10-30 seconds per wavelength, and involve mechanical movement of the filters and the use of a beam chopper and lockin (synchronous) amplifier that detects the electrical response. Additionally, variable neutral density filters or other mechanical apertures may be needed to control light intensity. With this measurement overhead, full spectra often take 5-10 minutes to cover the necessary wavelength range with sufficient resolution. This required mechanical motion also increases the cost and complexity of the instrument and makes it less suitable for a manufacturing environment.

The long measurement time of conventional QE systems prevents them from effectively being used in a mapping mode (10's to 1000's of data points per sample) to study localized or spatially varying effects. Also, the poor etendue of the conventional source sets a minimum practical measurement area, such that any reduction in measurement area below this value creates a further tradeoff of spatial resolution and measurement speed. Depending on the structural details and target application of the Device Under Test (DUT), it may be desirable to resolve millimeter spatial scales. To accomplish this a high-speed QE technique is required.

In one attempt to improve the art, an optical spectroscopy method was used to determine the quantum efficiency (QE) of a solar or PV cell, and the determination is performed in less than a minute. The system included a light source that produced multiple wavelengths concurrently and later independently processed them to determine QE at each of the wavelengths. The light source included an array of light emitting diodes (LEDs), rather than the standard white light source provided by a single halogen light bulb, for simulating the full spectrum of sunlight. A power source was used to individually drive each LED at its own unique operating frequency. The power source was a modulated power supply using a sinusoidal-wave modulated or a square-wave modulated power supply. The light source can also operate in the constantly ON mode too, where all or some of the LEDs are constantly on.

During the QE measurement of the solar cell, all of the LEDs in the array are driven "concurrently" to illuminate the solar cell. The AC current generated in the solar cell from the light transmitted by the light source was signal processed such that it was amplified and converted into a digital voltage signal (e.g., a signal made up of the individual signals corresponding to the unique operating frequency of each LED in the LED array). The use of sinusoidal power supplies expedited the use of a Fast Fourier Transform (FFT) module or algorithm run by a computer to determine the power spectrum of the current in the solar cell as a function of drive frequency from each LED light, where the voltage waveform associated with each operating frequency was converted into an amplitude associated with each drive frequency or LED. A reference cell was used to calibrate the amplitude of the FFT signals such that QE measurement module was run by the computer processor to calculate a QE value for each operating frequency or LED or light wavelength by applying a conversion factor obtained through use of the reference cell to each amplitude to generate and display a QE curve. Though this resulted in a reduction in the determination time, the resulting QE measurement included significant margins of error, due to poor spectral control of the LED light source and because light reflected, scattered or transmitted by the DUT was not measured and accounted for. Thus, the resulting QE determination provided no information relating to an internal QE value, which provides a most accurate measurement of the integrity of the DUT.

Accordingly, there is a need to develop a system for accurately and quickly measuring both a general QE and an internal QE that is low cost and easy to implement.

SUMMARY OF THE INVENTION

The present invention provides a high-speed Quantum Efficiency (QE) measurement device that includes at least one device under test (DUT), at least one conditioned light source having at least one filtered LED with a less than 50 nm bandwidth, where a portion of the conditioned light source is monitored by light source monitoring elements having at least one collection optic and at least one photo detector. The high-speed QE measurement device further includes delivery optics disposed to direct the conditioned light source to the DUT, a controller that drives the conditioned light source in a time dependent operation, where a response by each DUT from the conditioned light source is uniquely identified, and at least one reflectance measurement assembly having at least one reflectance collection optic and at least one photo detector disposed to receive a portion of the conditioned light that is reflected from the DUT. Additionally, the high-speed QE measurement device has a time-resolved measurement device that includes a current measurement device or a voltage measurement device, or a current measurement device and a voltage measurement device, where the time-resolved measurement device is disposed to resolve a current or a voltage, or a current and a voltage generated in the DUT by each conditioned light source. The high-speed QE measurement device further includes a sufficiently programmed computer disposed to determine and output an internal QE value for each DUT according to an incident intensity of at least one wavelength of from the conditioned light source and the time-resolved measurement.

In one aspect of the invention, the conditioned light source includes at least one conditioning optic disposed to reduce a bandwidth of the light source. Here, the at least one conditioning optic can include an optical filter, where an output from the conditioned light source comprises a less than 50 nm bandwidth.

In another aspect of the invention, the high-speed QE measurement device further includes an internal calibration sensor, where the internal calibration sensor comprises a sensor disposed to measure an intensity of the conditioned light source. Here, the internal calibration sensor can include at least one sampling optic and at least one sampling photodiode.

According to another aspect of the invention, the determined internal QE value from the sufficiently programmed computer includes parameters such as a charge on an electron, the reflected light from the DUT, a number of photons per unit time of the conditioned light source directed at the DUT, measured transmitted light from the DUT, measured transmitted and reflected light from the DUT, a voltage generated by the DUT when illuminated by the conditioned light source, and an electric current generated by the DUT when illuminated by the conditioned light source. Here, the output internal QE value can be a dimensionless quantity in a range of 0 to 1.

In another aspect of the invention, the high-speed QE measurement device further includes a transmission detection assembly having at least one transmission photo diode, where the transmission detection assembly is disposed to measure a fraction of incident the conditioned light source transmitted through the DUT.

In another aspect of the invention, the time-dependent operation can be pulsed operation or modulated operation.

According to embodiment the high-speed QE measurement device includes at least one DUT, a controller, at least one conditioned light source having the controller driving each conditioned light source in a pulsed operation, where a response by each DUT from each conditioned light source is uniquely identified, delivery optics, where the delivery optics direct the conditioned light source to the DUT, a time-resolved measurement device having a current measurement device, a voltage measurement device, or a current measurement device and a voltage measurement device, where the time-resolved measurement device is disposed to resolve a current, a voltage or a current and a voltage generated in the DUT by each conditioned light source, and a sufficiently programmed computer disposed to determine and output a QE value for each DUT according to an incident intensity of at least one wavelength of from the conditioned light source and the time-resolved measurement.

According to one aspect of the current embodiment, a first conditioned light source is pulsed at a first pulse duration and another conditioned light source is pulsed at another pulse duration.

In another aspect of the current embodiment, the conditioned light source includes at least one conditioned LED having an output bandwidth less than 50 nm.

The high-speed QE measurement device of the current embodiment further includes an internal calibration sensor having a sensor disposed to measure an intensity of the conditioned light source. Here, the internal calibration sensor includes at least one sampling optic and at least one sampling photodiode.

In a further aspect, the determined QE value from the sufficiently programmed computer includes parameters such as a charge on an electron, the reflected light from the DUT, a number of photons per unit time of the conditioned light source directed at the DUT, measured transmitted light from the DUT, measured transmitted and reflected light from the DUT, a voltage generated by the DUT when illuminated by the conditioned light source, or an electric current generated by the DUT when illuminated by the conditioned light source. Here, the output QE value can be a dimensionless quantity in a range of 0 to 1.

In another aspect of the current embodiment the high-speed QE measurement device further includes a transmission detection assembly having at least one transmission photo diode, where the transmission detection assembly is disposed to measure a fraction of incident the conditioned light source transmitted through the DUT.

In another aspect, the high-speed QE measurement device further includes a reflection detection assembly comprising at least one reflection photo diode, where the reflection detection assembly is disposed to measure a fraction of incident the conditioned light source reflected from the DUT.

In yet another aspect, a unique duration of the pulse is assigned to each conditioned light source, where a signal to noise ratio of each conditioned light source is normalized to other wavelengths.

In another aspect, a unique duration of the pulse is assigned to each unique conditioned light source from each conditioned light source, where the assigned pulses normalize a time-averaged intensity of one conditioned light source to another conditioned light source over a light spectrum useful to the DUT.

According to a further aspect of the current embodiment, a unique duration of the pulse is assigned to each wavelength from each conditioned light source, where the assigned unique pulse is disposed to optimize a signal to noise ratio of the conditioned light source at a desired wavelength.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Figure 1:
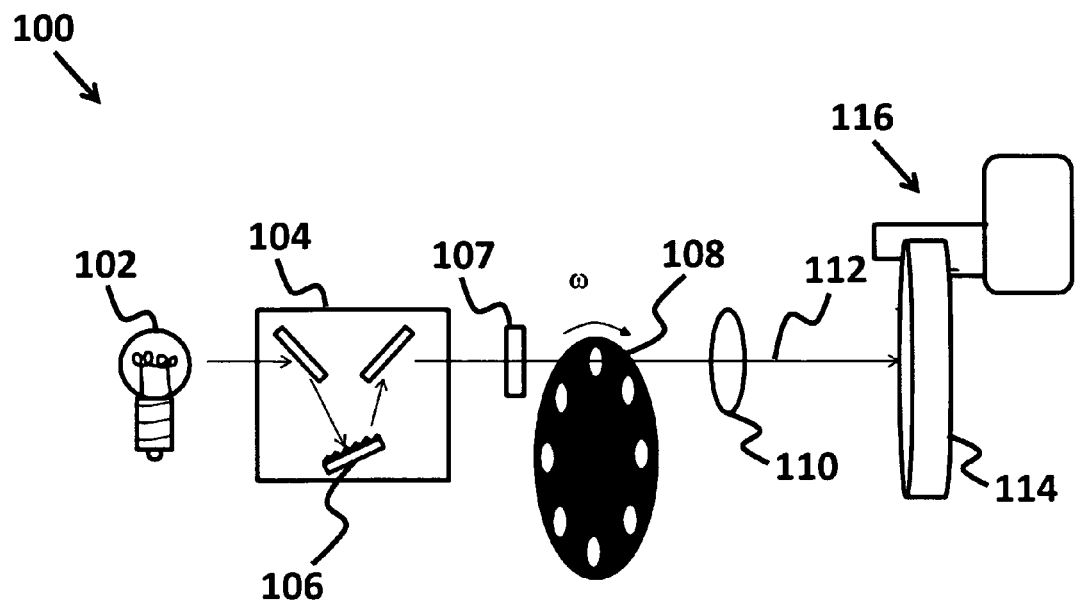
FIG. 1 shows a prior art QE measurement system.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

According to the current invention, the QE measurement applies also to the measurement of Responsivity or SR via a simple conversion of units. The current invention provides a high-speed quantum efficiency (QE) measurement device. In one aspect, the invention uses LED light sources, where commonly available LED's have LED output ranges that span from 300 nm to 1600 nm with approximately 10-50 nm spacing. The high spectral brightness (power per unit bandwidth per unit area per unit solid-angle) of LED's compares favorably with other more expensive conventional sources, while providing several additional benefits in the areas of wavelength stability, intensity stability, power consumption, ruggedness, modulation and pulsing capability and manufacturability.

The current invention includes a unique angular multiplexing scheme to improve the signal to noise ratio by separating the high-power DC bias light from the optic path of the pulsed lightsource, and a variety of sensors are introduced which allow real-time monitoring of incident intensity, specular reflectance, diffuse reflectance, and transmittance through the device under test (DUT). These aspects are combined into a single energy-efficient system capable of measuring a QE spectrum in approximately 1 second without moving parts or conventional broadband lightsources. The resultant device is compact and exhibits the measurement speed and durability necessary for use in a manufacturing environment.

According to the current invention, a solar cell is a device capable of absorbing incoming sunlight (photons) and delivering electric power to an external load. The more general term 'photovoltaic device' may be used interchangeably with 'solar cell.'

According to the current invention, a device under test (DUT) can include a solar cell or collection of solar cells connected in series, parallel, or a combination of the two. This collection may represent a manufacturer's 'module', a collection of modules, or a subset of cells within the module. The DUT can further include single, monolithically grown solar cell module (such as amorphous Silicon [a-Si] on glass substrate or Copper Indium Gallium Diselenide [CIGS] on steel, a photo detector or array of photo detectors, a photodiode or array of photodiodes, or a Charge Coupled Device (CCD) element or array.

According to the current invention, an LED can be any LED or array of diodes, including those based on inorganic and organic materials. Further, according to the invention, one or more of the LED's may be replaced with solid-state lasers.

Solar cell output parameters typically are measured as a function of temperature while the cell temperature is varied, for example in range 0-60° C. A single coefficient is derived to describe the change in each parameter including current, power, voltage and resistance as a function of temperature, which is used to predict the behavior of the cell at various operating temperatures. It is more beneficial to measure the wavelength dependence of the parameters, as well, to further characterize the degradation mechanisms. QE vs. temperature can be used to determine, for each wavelength of light, a coefficient that describes the change in cell power (or current, or voltage) as a function of temperature.

The current invention provides an array of LED's that are used to generate discrete narrow-band (typically <50 nm bandwidth) DC or pulse-modulated light emission. This array is called the 'lightsource' according to the invention. It is within the scope of the invention where one or more of the LED's contained in the lightsource may be replaced with laser diodes, solid-state lasers or conventional lamps (e.g.—quartz tungsten halogen lamp, arc lamp, or metal halide lamp). A time dependent signal is used to stimulate emission from each LED so that the response of the DUT to each wavelength of light may be uniquely determined via properly timed data acquisition of the cell current (or voltage) output. In one aspect of the invention, a sequential (and non-overlapping) pulsing of many LEDs can be implemented.

The invention includes one aspect in which each LED is pulsed for a predetermined period of time and with a predetermined drive current, such that the total duration of the sequence is minimized and that the observed signal-to-noise ratio is adequate across the full spectrum of the measurement. The operating condition (drive current and pulse duration) of each LED is chosen so that the device is operated without suffering damage (the operating limit of each LED depends on manufacturing details of the device and thermal considerations that are greatly reduced by the low average duty cycle). According to the invention, it is advantageous to maximize the current level (and therefore light output) for each LED. The duration of the pulse for each LED will depend on the current level, and also on the electrical-to-optical efficiency of the LED, the coupling efficiency from the LED to the system (determined primarily by the etendue of the LED, which is in turn determined primarily by the die size), and the detection characteristics of the reference photodiodes at the wavelength of that LED.

In one aspect, where the response time of the DUT's electrical output to a light pulse is limited by RC effects (typical of a large area, high capacitance solar cell), a method wherein the DUT RC attenuation factor is measured once for each sample or sample type by acquiring a dataset of the cell current output amplitude vs. light pulse width or modulation frequency. The ratio of long pulse (DC behavior) to short pulse (high-throughput mode) response amplitude may then be used to correct all subsequent short pulse measurements so as to calculate the expected DC behavior. As an alternative, a step-function current pulse or modulation frequency sweep may be applied to the LED while measuring the time-resolved current output of the device to yield similar results.

The optimal wavelength range of the light source is tailored to the intended operating environment and material type of the DUT. For solar applications, the shortest wavelength is usually determined by the incident spectrum (e.g.—AM0 [space], AM1.5 [terrestrial], etc.), while the longest wavelength is determined by the lowest band gap active material used in the device. Wavelength ranges might be chosen per application such as crystalline silicon terrestrial applications 400 nm-1100 nm; crystalline silicon space applications 300 nm-1100 nm; copper Indium Gallium Diselenide terrestrial applications 400 nm-1250 nm; and III-V multijunction cells, such as the AlInGaAsP family, space applications 300-1800 nm.

Figure 2:
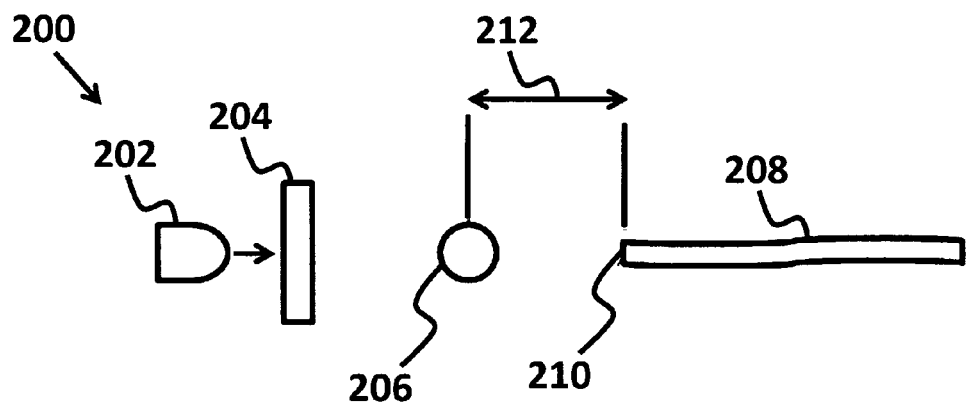
FIG. 2 shows an arrangement of a conditioned light source and delivery optics.

According to the invention, individual narrow bandpass filters are placed in front of each LED to filter the emitted light. FIG. 2 shows an arrangement of a conditioned light source and delivery optics 200, where shown are an LED 202, a dielectric bandpass filter 204, shown at an arbitrary tilt angle, a ball lens 206 disposed to focus collimated light onto a fiber 208 having a fiber end face 210, where the spacing 212 between ball lens 206 and fiber face 210 is equal to the focal length of the ball lens 206.

Note that filters 204 used in this LED-based application are not expected to suffer from rapid degradation because the incident light intensity from a single LED 202 is well below the damage threshold of most filters 204. In addition, the spectral output of the LED 202 and filter 204 system is insensitive to filter transmission 'leaks' that occur at wavelengths significantly removed from the peak LED emission wavelength; filter leaks are not a concern in wavelength regimes where the emission intensity is zero, as illustrated in FIG. 3.

Figure 3:
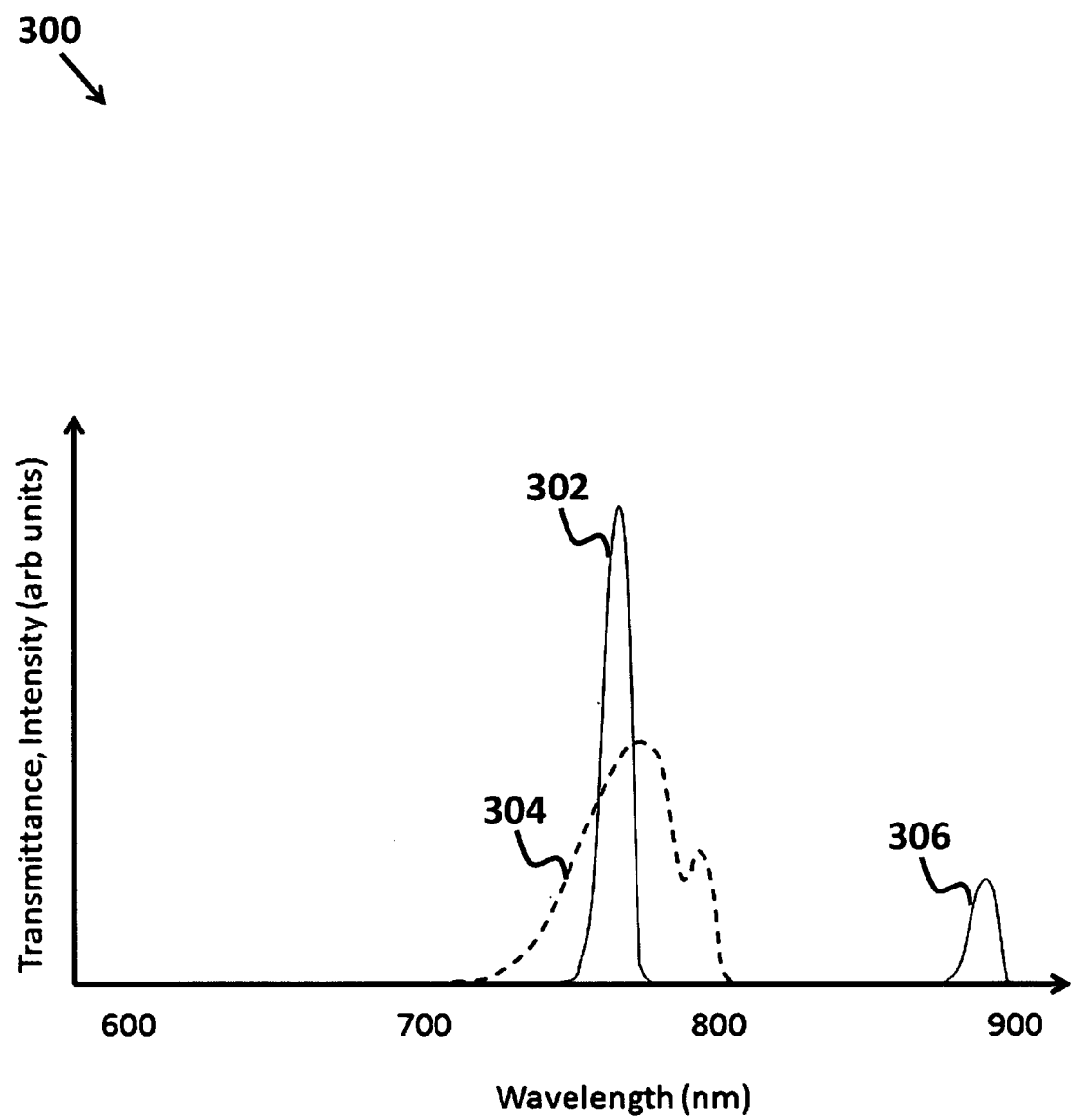
FIG. 3 shows a graph of the relaxed filtering requirements when using an LED or other narrow-band lightsource according to the present invention.

FIG. 3 shows a graph of the relaxed filtering requirements 300 when using an LED or other narrow-band lightsource, where shown is the transmittance curve 302 of the filter in use, the Intensity curve of the LED 304 in use, and filter light leakage 306 that occurs at a wavelength well-separated from the LED 304 emission peak. This light leakage has no impact on the spectral output of the lightsource, since there is no LED emission in this wavelength regime.

In one aspect of the invention, the filter is used to remove the effect of wavelength drift that occurs during LED warm-up or cool-down, or to variations in ambient temperature. Further, the filter is used to remove the slow drift in peak emission wavelength caused by long-term aging of the LED, or to remove LED batch wavelength variability that is often observed in poorly-toleranced LED manufacturing processes. According to the invention, the filter is used to narrow the spectral bandwidth of the LED by rejecting emission outside of the filter bandpass. This is particularly useful on the large number of LED's that exhibit spectral widths in the 20 nm-100 nm range, rendering the LED more usable for spectroscopic applications. Further, the filter is used to select portions of the broad LED emission spectrum so that a single type of LED may be used to generate several distinct, non-overlapping wavelengths of light. The filter can include ion beam sputtering technology used to create the (bandpass) interference filters that are appropriate to the invention, because this deposition technique yields films that are robust and relatively immune to temperature-induced drift. In one aspect, other filters are useful such as color filters (either color glass or polymer dye) or gratings, and combination of long-pass, short-pass and bandpass filters may be used to achieve the filtering benefits described here.

Filters that are of a relatively simple multilayer design are used because the LED light source comes reasonably close to generating the ideal narrow bandwidth spectrum even without a filter. This removes the requirement for broad stopbands (as would be the case for use with a traditional broadband light source) that drives up the filter design complexity in traditional lamp-based systems. The limited wavelength range of LED emission further minimizes the requirement for passband shape (i.e. square shape is not required) and there is only a modest requirement for how strongly the stopbands are attenuated (99% attenuation is ideal, while 90% is adequate. Such a configuration is significantly less stringent than for a traditional lamp-based system). In one aspect, the filter arrangement can include two identical quarter-wave stacks that are separated by an odd number of quarter-waves of spacer/material (ideally one of the same materials that are used in the stacks). The number of layers in the quarter-wave stacks determines the bandwidth of the passband, as well as the attenuation level in the stopband. Because the deposited layers are fairly thin (for an interference filter), this type of filter design operates efficiently over a wide range of incidence angles.

Figure 4:
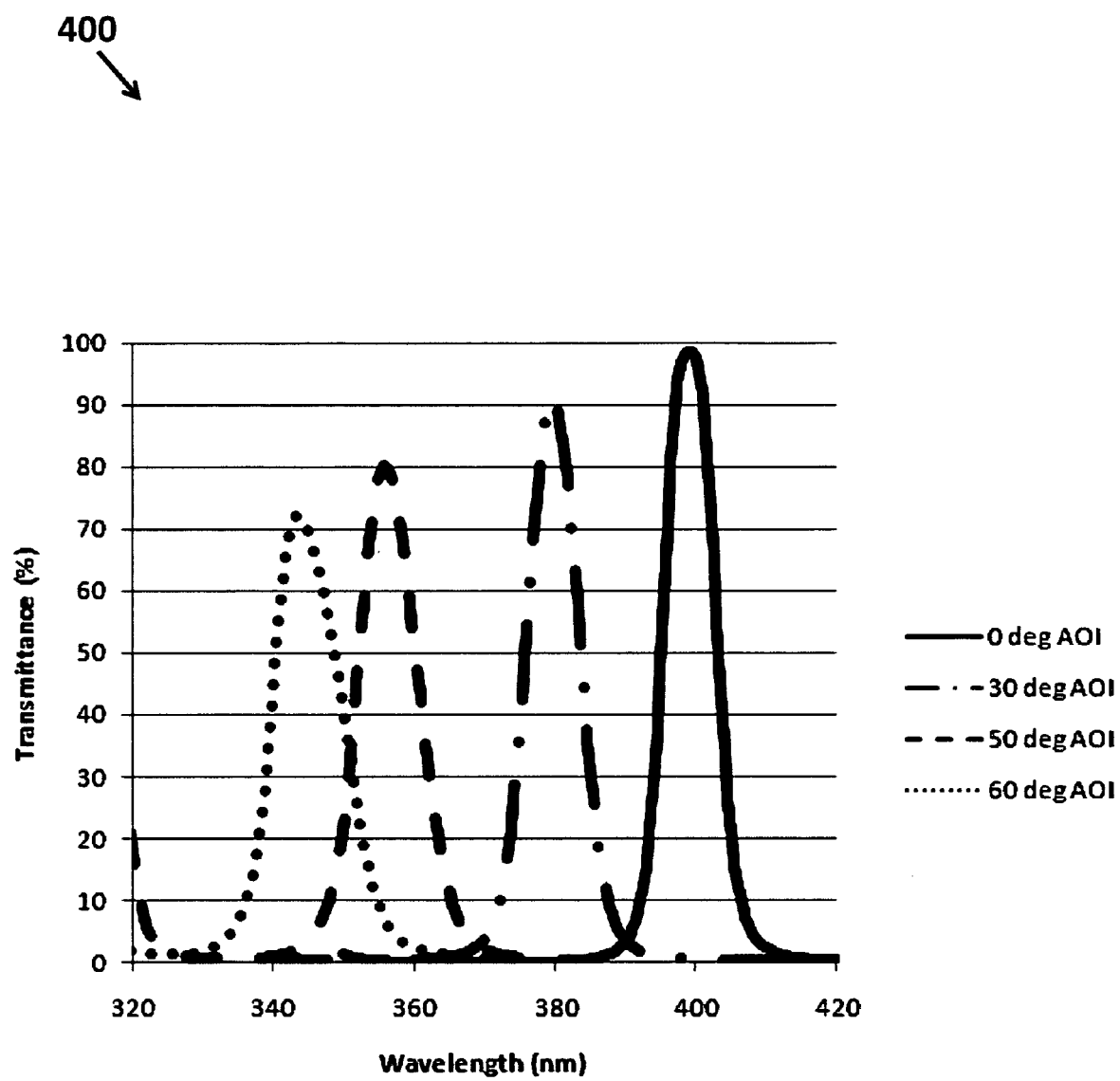
FIG. 4 shows a graph of transmittance of a dielectric interference filter, plotted as a function of tilt angle according to the present invention.

In one aspect of the invention, the bandpass filters are tilted to blueshift the peak transmission wavelength with only a moderate effect on the transmission coefficient and bandpass width. FIG. 4 shows a graph of transmittance of a dielectric interference filter 400, plotted as a function of tilt angle (AOI=Angle of Incidence, in degrees). This technique allows a single filter part to be used for precise bandpass control at multiple wavelengths, thus reducing system design complexity and cost. This concept is particularly effective when used with the simple quarter-wave-stack-based interference filter design described above.

Referring to FIG. 2, the invention includes a device in which a lens 206 is placed after the bandpass filter 204, and is located one focal length 212 from the end 210 of an optic fiber 208. This lens-to-endface dimension is critical to the design, such that when the ball lens 206 is located one focal length 212 away from the fiber endface 210, only collimated rays entering the ball lens 206 are coupled into the fiber 208. Hence, only collimated rays passing through the bandpass filter 204 will be coupled into the fiber 208. This preserves the narrow bandpass property of the interference filter, since the peak transmission wavelength is a function of the angle between the incident light wave-vector and the surface normal of the filter.

Figure 5:
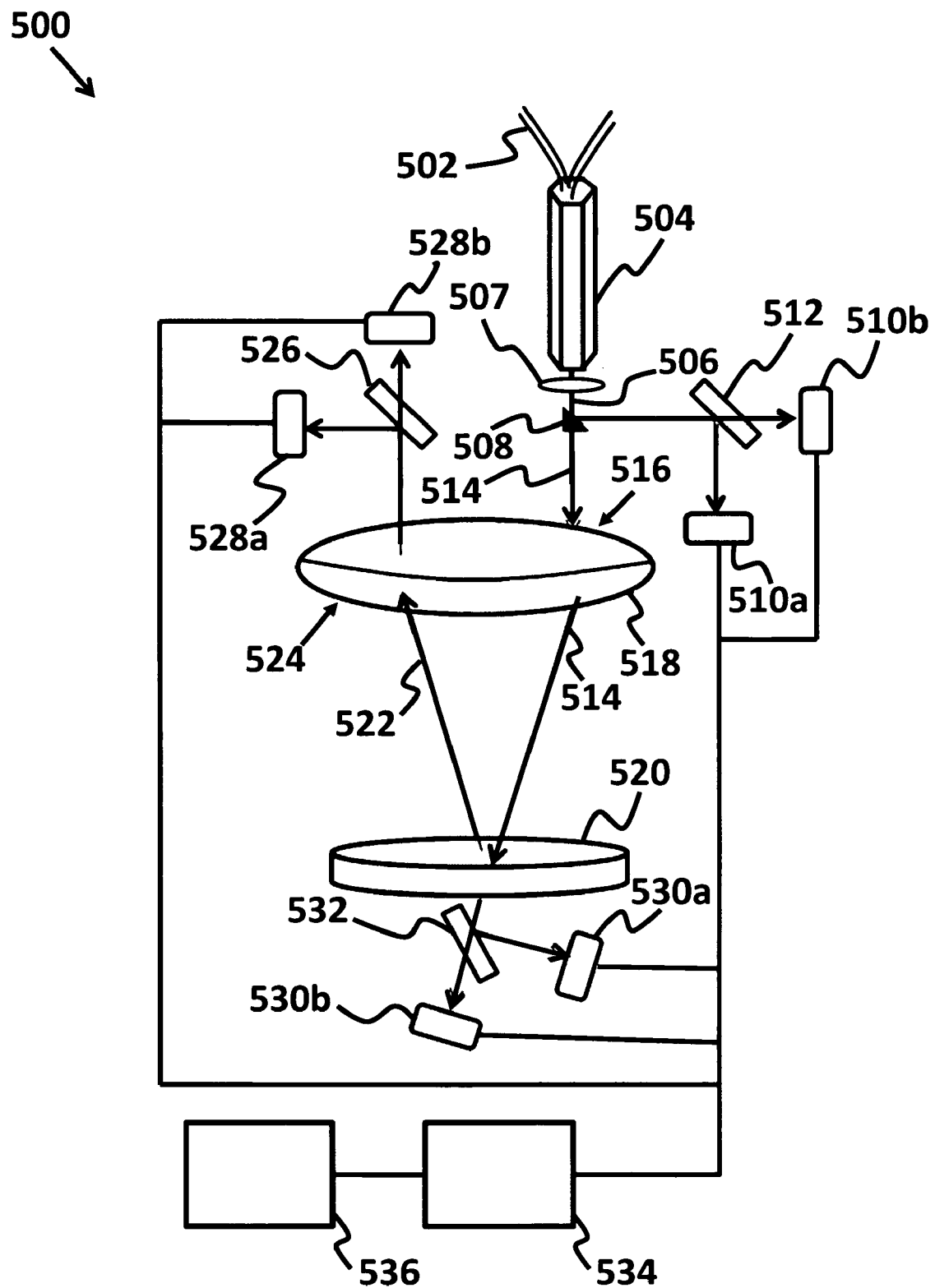
FIG. 5 shows a schematic diagram of lens assembly and intensity monitoring scheme according to the present invention.

The invention can include a device in which individual fibers, each delivering one or more sources of narrow-bandpass light, are collected into a close-packed bundle and the end is polished to improve transmission properties. One or more bundles are then coupled to an optical element, for example a UV-grade fused silica hexagonal lightpipe, which homogenizes the spatial uniformity of the beam before delivering it to focusing optics. FIG. 5 shows a schematic diagram of lens assembly and intensity monitoring scheme 500 according to the current invention. As shown, individual fibers 502 from the LED light source (see FIG. 2) deliver photons to the top face of a homogenizing device 504, such as a lightpipe. A spatially uniform beam 506 exits the homogenizer 504 and is sampled by a small reflective optic 508 (or fiber) to capture a fraction of the incident light and direct it to a pair of photodiodes 510(a)/510(b) via a partially reflective optic 512 in order to monitor the incident light intensity. The unsampled portion 514 of the beam 506 is directed onto quadrant (I) 516 of the aspheric lens 518. The unsampled portion 514 of the light is partially reflected from the DUT 520, and the reflection 522 is directed to quadrant (III) 524 of the asphere 518. A beamsplitting optic 526 is used to direct light to two reference photodiodes 528(a)/528(b) that measure the reflected light intensity. A separate detector pair 530(a)/530(b) and beamsplitting optic 532 are located below the sample 520 to detect light transmitted by the DUT 520. Note that additional photodiodes may be added to monitor the diffuse components of both reflected light and transmitted light. As mentioned above, other methods of wavelength combining and beam homogenization can be used, such as integrating spheres or tapered lightpipes. Further shown is a time-resolved measurement device 532 that can include a current measurement device and/or a voltage measurement device. The time-resolved measurement device 534 is connected to a sufficiently programmed computer 536 disposed to determine and output an internal QE value for each the DUT according to the incident intensity of at least one wavelength from the conditioned light source and the time-resolved measurement. It is understood that the sufficiently programmed computer 536 can include analog/digital electronics.

The reflective optic 508 used to sample a fraction of the beam 506 after it exits the lightpipe 504 is directed to one or more reference photodetectors 510(a)/510(b) to provide real-time measurement of the incident light 514 intensity. As shown this same technique may be used to monitor light transmitted through the DUT 520, as well as light reflected 512 specularly or diffusely from the sample 520. Regarding the reference photodetectors to measure incident light intensity, the detectors are selected so that they provide sufficient spectral sensitivity (covering the range from the lightsource's shortest to longest wavelengths). For example, two photodetectors (Si and InGaAs) can be used to provide spectral sensitivity from 300 nm to 1700 nm.

The focusing optics 507 are used to direct the main beam 514 to an off-axis position 516 of the high-NA aspheric lens 518. The beam is partially reflected from the sample and returns through off-axis position 524 of the asphere 518. This off-axis placement of the incident beam 514 creates an 'angular multiplexing' effect so that incident 514 and reflected beams 522 can be spatially separated to minimize crosstalk and allow room for detectors without the need for further beamsplitting optics. Reflectance detectors 528(a)/528(b) are placed in off-axis position 524 above the aspheric lens 518 to intercept this reflected light 522. Additional detectors may be added to detect and discriminate between specular and diffuse reflections. An further benefit of angular multiplexing is the ease with which it enables DC light bias to be used to study or quantify carrier trapping behavior in photodetectors, solar cells and other optoelectronic devices. The light from these sources must be somehow blocked or compensated so that does not interfere with (for instance, saturate) the photodetectors which are used to measure the various components of reflectance and transmittance. In this invention, bias light sources, which may include conventional broadband light sources, lasers, or bright LED's, are explicitly included in the design and are directed into Quadrant II of the asphere 518: in this case the specularly reflected beam is directed into Quadrant IV of the asphere 518. Alternatively, two bias light sources can be supported, one occupying Quadrant II and one occupying Quadrant IV. This arrangement has the significant benefit of minimizing the amount of bias light that is scattered into the reflectance monitoring (Quadrant III) photodiodes. This technique thus utilizes 'angular multiplexing' to allow a single asphere to deliver multiple lightsources to a single point on the DUT while minimizing unwanted signal mixing between the various detection channels.

Additional detectors 530(a)/530(b) are placed below the sample 520 so that the sample transmittance can be monitored at each wavelength. Additional detectors may be added to detect and discriminate between specular and diffuse (scattered) transmission. The photodetectors 530(a)/530(b) placed below the plane of the sample are used to measure the fraction of light that is transmitted through the sample. This is of particular interest for thin solar cells that are designed to allow partial transmission for building-integrated lighting. In this case, the transmitted light must be accounted for in the calculation of QE, and provides an important control parameter for the manufacturing process because it is directly observable by the end-user.

Bifacial solar cells are essentially two separate photodetectors facing in opposite directions. The rear cell may be used to collect weak reflected albedo from under photovoltaic arrays and boost total power output of the device. In this configuration (as well as others), it is important to measure the QE from both the front and the backside of the cell. Measurement speed is paramount in a manufacturing environment, and a 'twinned' version of the solid state QE apparatus described above may be used to measure front and backside QE in rapid succession. In this configuration, one measurement head is oriented to face the cell from the front side, and the second measurement head is oriented to face the cell from the backside. A single computer or control system is used to coordinate the light pulses or modulation frequencies from both heads so that they do not unintentionally interfere or overlap in time. It should be apparent that an arbitrary number of QE measurement heads may be used and are within the scope of the invention.

With the integration of the QE head or heads onto a system, either the measurement head(s) or sample may be placed on a goniometer positioning stage so that the QE can be measured as a function of angle of incidence. In head orientations for which the angle of incidence is other than normal, the partially-reflected power will not automatically be aligned to the reflectance detectors. Therefore, adjustable mirrors, lenses or fibers may be used to capture the reflected light, where the elements are positioned relative to the incident beam by placing them symmetrically about the sample surface normal. In cases when the reflectance information is not necessary, the system as can be used with the measurement head held at a non-normal angle of incidence.

According to one aspect, the system may be operated in a mode in which a plurality of LED's with a variety of emission wavelengths are energized simultaneously so that a reasonable approximation of the solar spectrum is created and focused onto the DUT. For example, the amplitude of the current delivered to each LED is individually controlled so that the spectral content of light can be modified to closely match a target spectrum such as AM0, AM1.5, or an arbitrary combination of airmass, time of day, latitude, and cloud conditions. A spectrometer can be used to analyze the spectral content of the emitted light and the information is used to tune the individual LED currents until the output spectrum is within a predetermined tolerance of the target spectrum, as well as calculate, in real time, the spectral mismatch factor. The current invention enables the spatial extent of the illuminated area to be known or measured, and for the light intensity to be known or measured. This information is used to calculate (in conjunction with a measurement of the cell current-voltage characteristics) the 'illuminated' or 'light-biased' J-V characteristics of the cell, where these characteristics include, among others, the open circuit voltage, short circuit current, maximum power point, and device conversion efficiency for the specific incident spectrum used during the test.

According to the invention, the system combines the QE and solar simulation capabilities described above, so that both the QE and illuminated J-V properties of devices can be measured in rapid succession on a single tool. This system, when combined with a measurement stage such that the measurement head, sample, or both may be translated, allow spatial mapping of quantum efficiency. The measurement head may also be mounted on a goniometer to allow scanning by rotating the head. In one aspect, the system described above may be combined with a variable aperture device so that the measurement spot size can be controlled to allow adjustable spatial resolution and measurement throughput. In one aspect this arrangement would dispose the aperture at the exit of the lightpipe, as this location is re-imaged onto the DUT.

In another aspect of the invention, a recipe-based computer control system is provided so that automated analysis may be performed on a series of measurement sites, and when combined with automatic loading, automated analysis may be performed over a set of samples. This aspect may be combined with a deposition or processing tool so that QE measurements may be performed either during actual cell processing or prior to removing the sample from the processing environment. This may be further combined with a current-voltage (J-V) tester and solar simulator so that cell performance binning (sometime called sorting) may be performed according to J-V characteristics, QE characteristics, or a combination of both. A further aspect can include a current-voltage (J-V) tester and solar simulator, optionally a photoluminescence or electroluminescence measurement, and optionally an infrared 'hot-spot' defect imaging system so that performance binning may be performed according to J-V characteristics, QE characteristics, luminescence characteristics or infrared defect characteristics, or a combination of any of these characteristics. Another aspect includes the current embodiment combined with a camera-based inspection system so that performance binning may be performed according to all of the techniques listed above, as well as the optical inspection results (wafer chips or cracks, anomalous reflectance characteristics (color) or uniformity, improperly formed electrical contacts, or other physical imperfections). Here, a camera can be coaxially mounted so that the spot under test can be visualized in real-time.

According to one variation, the system described above can be implemented using optical components that are transparent through the entire wavelength range of interest (UV to near-IR). For example, UV-grade fused silica can be used for the lightpipe and for all subsequent lenses, including the asphere. Alternatively, calcium fluoride can be used for the asphere/objective. As one alternative, sapphire can be used for various lenses. As a second alternative, a combination of UV-grade fused silica, sapphire and calcium fluoride can be used to cancel the effects of chromatic aberration. In one embodiment, sapphire ball lenses are used to couple light from the LED into the multimode fiber. According to this aspect, the optical fiber material is chosen optimally for each wavelength in the array of LEDs. For example, UV-grade fused silica fiber is used for wavelengths shorter than 800 nm, and IR-grade fused silica fiber is used for wavelengths longer than 800 nm. The exact choice of wavelength cutoff is not critical to the design.

In a further variation of the invention, the invention is part of a multichannel system, which can collect QE data from multiple points on a DUT in which each channel uses a unique time dependent signal to stimulate emission from each LED, so that the response of the DUT to each wavelength of light and at each point may be uniquely determined via properly timed data acquisition of the cell electrical output. This aspect may be combined with stages or goniometers as described above to allow mapping. For example, a set of measurement heads arranged in a linear array may be used to scan in a direction normal to the array to generate a two-dimensional QE map.

The invention includes incorporation of QE data from the instrument into a yield management system. Further, the invention includes correlation of QE data with device performance, so that QE may be used as an early predictor of specific device problems, both electrical and physical in nature, or as a means of binning and sorting devices so that they can be combined to maximize module yield under specific illumination conditions.

In another variation, the invention includes the use of QE or illuminated J-V data to provide spatial coordinates to be used by a subsequent review or failure analysis system to further characterize regions of interest. Review or failure analysis systems may be, but are not limited to, the following types of tool, Focused Ion Beam, Scanning Electron Microscope, Optical Microscope, Time of Flight Mass Spectrometry, optical camera, optical defect scanning system, surface profilometer, ellipsometer, or laser beam induced current. Further, the use of the QE or illuminated J-V aspect can be in-situ in either a processing tool or failure analysis system to provide single point or mapping capabilities of QE in conjunction with other diagnostic information. The invention can include incorporation of a sample or samples with known QE into the DUT holder or measurement chamber to calibrate the accuracy of the device described above.

The above invention describes using the FFT power spectrum $\sqrt{(real)^2+(imaginary)^2}$ without phase information, but one could fit twice the number of LEDs into the same frequency space by phase-shifting the drive signal of half the LED's by 90 degrees. Then, the invention can use the Real and Imaginary results of the fast Fourier transform (FFT) to distinguish between the two sets of LED's. This is enabled because the phase of the modulation of each LED can be controlled. The two quadrature phases are orthogonal, and hence do not interfere in an FFT analysis. FFT analysis naturally results in both real and imaginary terms for each frequency. Additionally, random noise processes will equally distribute the noise power onto the two quadrature phases. If both phases are not used for LED modulation, then half of the noise at any given frequency can be eliminated by only measuring the "known-correct" phase that corresponds to the modulation of the corresponding LED. This results in a $\sqrt{2}$ improvement in the S/N ratio for the measurement. Since the modulation phases may be shifted with respect to the measurement "time-zero" reference, as described below, it may be necessary to apply a 2×2 matrix "rotation" operation to the measured FFT data so as to enable extraction of the in-phase and quadrature-phase information, prior to zeroing-out the quadrature phase signal.

In a perfectly linear system, it does not matter what frequencies and phases are selected for each of the LED modulations, as the (linear) FFT operation will extract the desired information. However, many aspects of a real system exhibit small nonlinearities (saturation of amplifiers, limited dynamic range of components, etc. . . . ) that may lead to artificial signals that are confused with real measurements. The error introduced by these nonlinearities can be influenced by the exact selections of modulation frequencies and phases. When all LEDs are modulated in a sinusoidial fashion, the peaks and troughs of their light outputs may or may not ever coincide to generate high instantaneous optical powers. Under these conditions, the nonlinear generation of spurious frequencies will be enhanced. It is, thus, preferred to avoid this situation. As described below, a poor choice of modulation signals would be evenly spaced frequencies with constant or evenly spaced phases. Chirped or randomly distributed frequencies and/or phases reduce the peak optical amplitude, and thus, reduces the nonlinear mixing of frequencies to generate spurious signals. It is the goal of the above considerations to ensure that the nonlinearities generate spurious signal levels that are smaller than the other sources of noise, such as shot noise.

Figure 6:
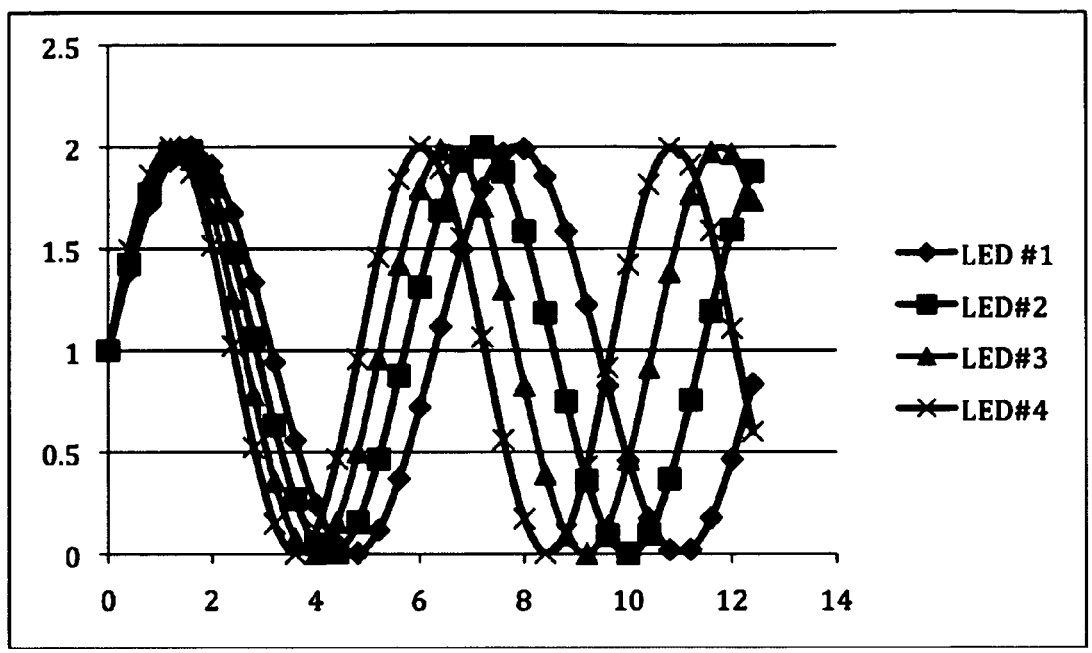
FIGS. 6(a)-6(b) show how uniform spacing in frequency and phase results in bunching according to the present invention.
Figure 6:
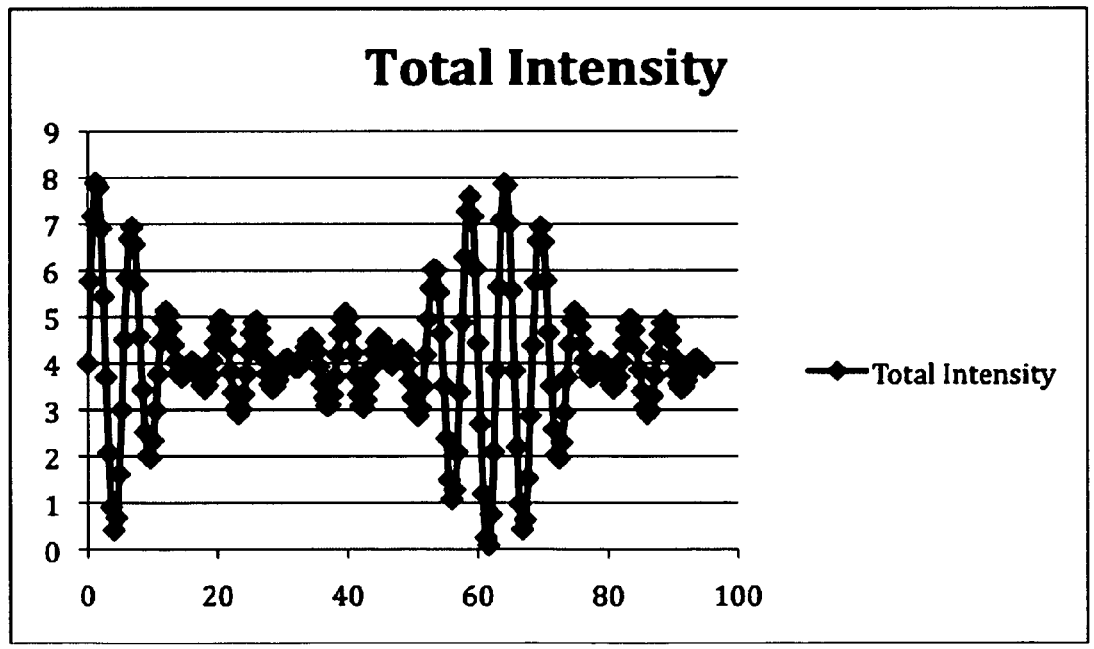

FIGS. 6(a)-6(b) show graphs of uniform spacing in frequency and phase results 600 in bunching, similar to mode-locking in lasers. In FIG. 6(a), the four colors represent 4 different LEDs, with frequencies of 1, 1.1, 1.2, 1.3. All are in phase at time=0. In FIG. 6(b), the total optical intensity shows peak-to-peak amplitude that is 4× higher than for a single LED. This scenario scales with the number of LEDs.

Figure 7:
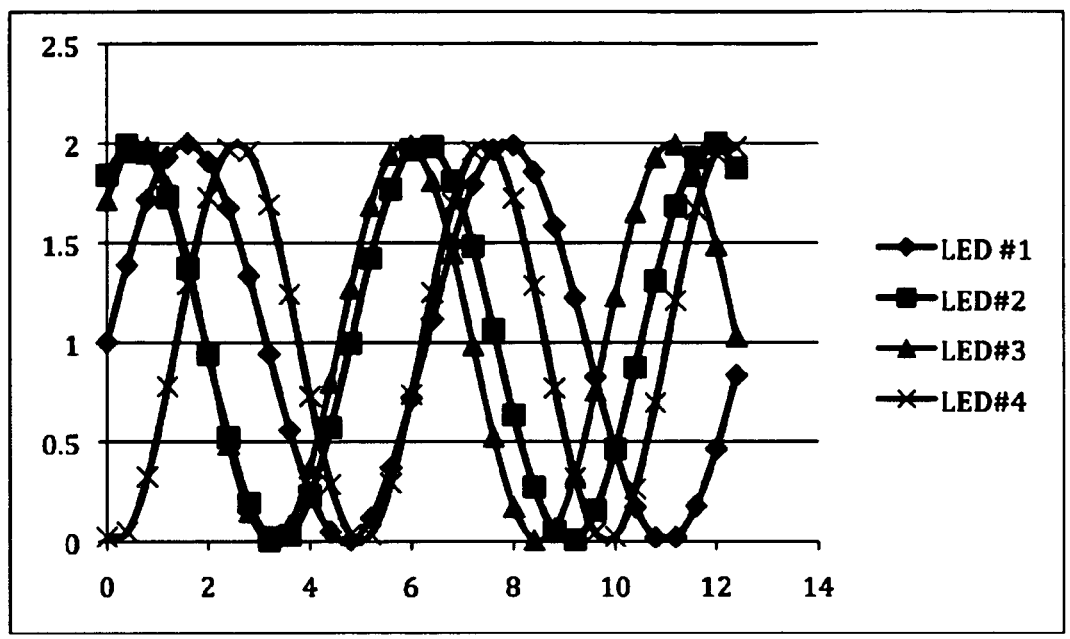
FIGS. 7(a)-7(b) show how uniform spacing in frequency and pseudo-random phase, results in reduced bunching according to the present invention.
Figure 7:
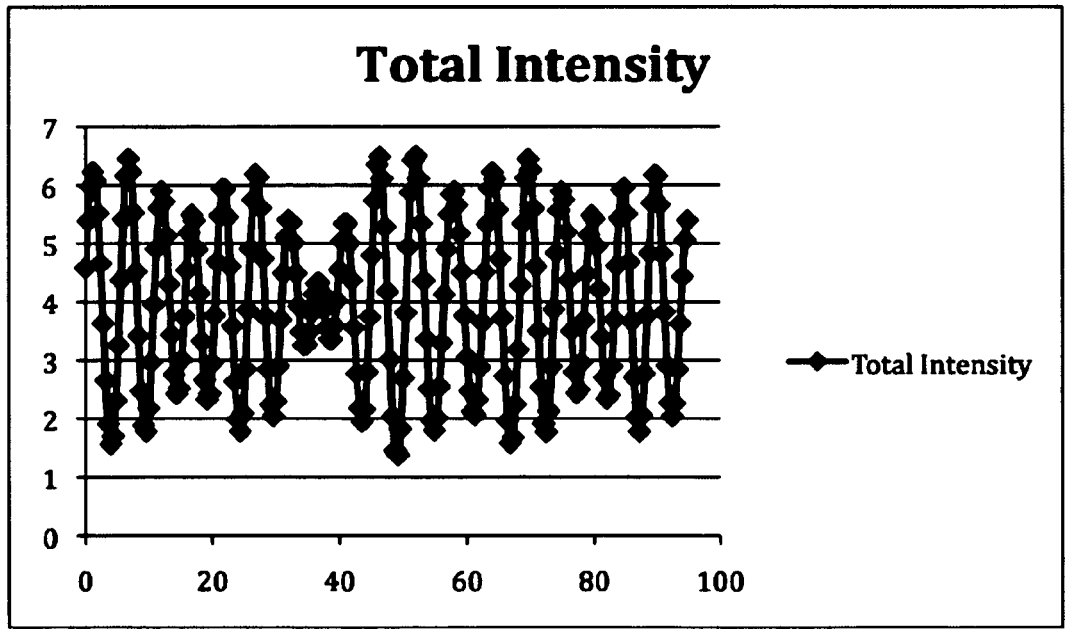

FIGS. 7(a)-7(b) show how uniform spacing in frequency and pseudo-random phase results 700 in reduced bunching. In FIG. 7(a), the four colors represent 4 different LEDs, with frequencies of 1, 1.1, 1.2, 1.3. They are never all in phase. In FIG. 7(b), the total optical intensity shows peak-to-peak amplitude that is about 3× higher than for a single LED. This scenario improves with the number of LEDs, as better averaging occurs.

Figure 8:
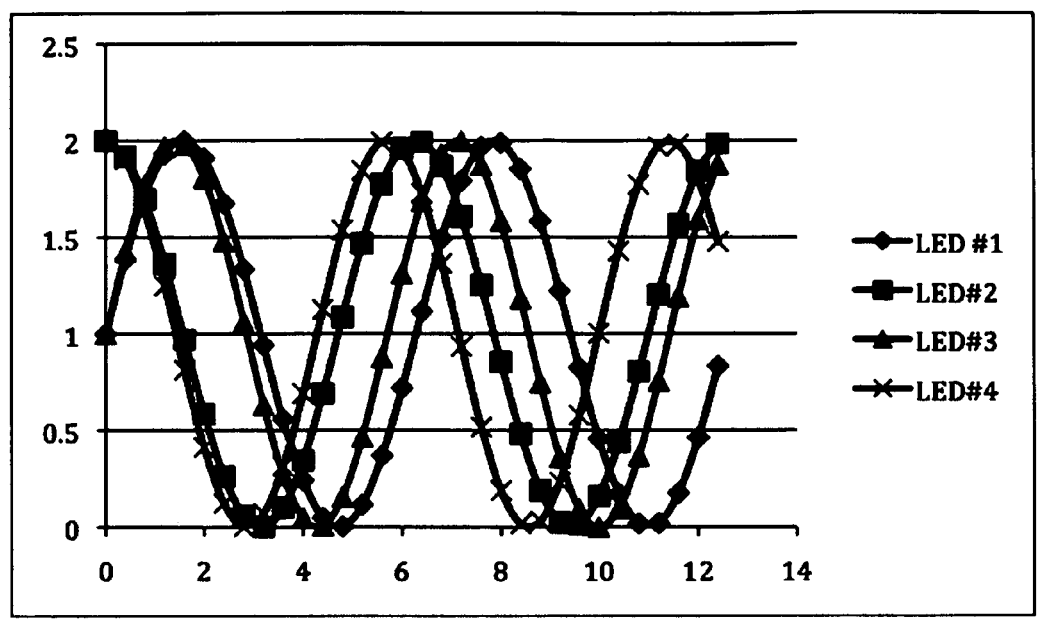
FIGS. 8 shows how two frequencies with both phase quadratures can be more densely packed in frequency according to the present invention.

FIGS. 8 shows how two frequencies with both phase quadratures can be more densely packed in frequency 800.

According to the current invention, the light incident on a solar cell can be divided up into direct and diffuse (light scattered from the sky, nearby buildings, or clouds). Diffuse components can be simulated by adding additional 'flood' or high-angle-of-incidence light sources to simulate a variety of diffuse conditions and measure the conversion efficiency under these illumination conditions [direct, diffuse, or any mixture of direct+diffuse]. In one aspect, the LED's can be modulated using other methods. For instance, using a code division multiple access (CDMA) technique to improve immunity to background noise.

In another aspect, "single-pulse" measurement, as distinguished from an AC modulated lightsource, may be used. This falls under the general concept of time division multiple access (TDMA) i.e. doing one thing at a time. The advantages of the single-pulse include simple and cheap electronics implementation that is easy for a microcontroller to sequence the pulses and acquire data, low injection level such that only one LED is running at a time and minimizes the incident power, this is useful when looking for the low-light performance of the cell, which is controlled by carrier traps. Further advantages include the ability to tailor the pulse duration per LED to achieve the desired signal to noise ratio. Some LED's emit very little light, so these would require a longer pulse. We would 'budget' the time to achieve the desired throughput, while achieving approximately equal S/N on every LED.

Another example of TDMA includes turning on one LED and modulating the output to do an FFT on DUT current to solve for QE, move to the next LED, and repeat the process. This combines the noise rejection of FFT's with the low injection level of pulses.

Another example of using pure phase information includes the modulated QE measurement is extended to a DC stepped method, where each LED may be turned on in sequence, resulting in a staircase function of cell current. The height of each step may then be analyzed to determine the incremental increase in cell output vs. wavelength. This is an example of using pure phase information to discern the response at each wavelength.

In one variation of the invention, a non-contact surface potential (Vs) sensor is included into the tool. This sensor is fixed above the cell, and in some cases below the cell if the cell has a back junction. Examples of a noncontact surface potential measurement include vibrating Kelvin probes (for DC surface potential measurements), rotating or oscillating Monroe probes for DC surface potential measurements), and transparent capacitive plates, also called surface photovoltage sensors (for AC surface potential measurements). The DC surface potential measurement may be used when local QE results are controlled by both the local material properties, as well as the resistance encountered when the photogenerated carriers are transported out of the device. Often, a researcher would like to remove the resistance effects in order to study only the local material properties. QE measurements may be intentionally performed at high DC reverse bias to enhance carrier transport from deep in the cell, or high DC forward bias to simulate the carrier density that the cell will experience under high illumination conditions. In each of these cases the resistive drop should be measured and accounted for. Also, the user may be interested in viewing a map of resistance vs. x-y position on the sample. The current embodiment uses the DC Vs measurement to measure the potential drop between the point of contact to the cell, that is the location that the probes touch the cell, and the location of the QE measurement. The two DC measurements are subtracted to determine the potential drop between the two locations. This differential measurement has an important additional effect, where it removes the drift typical in this type of Vs measurement that is due to humidity or any chemicals with dipole moment that may be adsorbed on the sensor surface. This Vs information can also be mapped for a constant photocurrent or bias condition, the potential drop can be used to calculate the resistance between every measured site and the contact point. This type of information can be used to detect variations in emitter or transparent conducting oxide sheet resistance and used to deliver emitter current to metal collection grids that often occur during manufacturing. In one aspect the surface potential (either DC or AC) may also be used to sense the presence of localized shorts (often called 'shunts') in the solar cell by applying bias voltage to cell, to enhance Vs signal difference between 'good' and 'defective' areas of the solar cell, mapping a surface potential by rastering the sample underneath the Vs sensor and recording the results as a function of position—a local reductions in surface potential will indicate defective areas of the cell, this aspect can be improved by adding additional probes to improve throughput such as a 1D array scanned in one dimension or 2D array.

A requirement for minimal crosstalk between drive channels is for the (N−1) channels other than the one being considered, the sum total of the crosstalk must be less than the allowable noise/uncertainty for the measurement. As an example, if there are 101 channels/wavelengths, and the desired measurement accuracy is 1%, then each channel may only leak 0.01% of modulation current onto any of the remaining channels. $(0.01\% = 1\% \ast (101-1=100)^{-1})$.

It is not important if a small amount of light from one LED leaks into the fiber that delivers light from another LED, because these two optical signals will be re-combined at a later position in the optical system (i.e. the Lightpipe), but before the pickoff used for calibration purposes. However, the light that does not go through the bandpass filters at the desired angle of incidence and will have a poorly controlled spectrum. If this light leaks into an adjacent channel's fiber, then this will reduce the effective spectral resolving power. However, this only matters to the extent that the LED bandwidth exceeds the desired measurement resolution. Typically, the LED bandwidth is about 2× the desired measurement resolution, so this is not a major concern.

Because of their large capacitance and finite resistance, solar cells exhibit limited frequency response, which typically rolls off at 0.5-8 kHz, depending on cell size and design. To limit simultaneously modulated LEDs to within an octave such as 200-400 Hz or 400-800 H and avoid mixing the FFT harmonics, the operating octave should be chosen to span sufficiently low frequencies that the cell has reasonable response over the frequency range, for example 0.1-1× the DC response. Within this constraint, the octave should be chosen to be at as high frequency as possible to maximize measurement throughput, according to the current invention.

To maximize measurement throughput, the frequency range may be chosen so that the cell exhibits attenuated response at the modulation frequencies. This effect may be calibrated prior to the measurement either on each cell, or at scheduled service intervals, or whenever the user chooses to perform the calibration. This is accomplished by using one LED and measuring AC cell current output while the modulation frequency is varied from near DC, for example near 10 Hz which is well below the attenuated region, to the desired maximum frequency. The data of response amplitude vs. frequency is then used to normalize subsequent measurement results. Interpolation or extrapolation is used to calculate the best estimated calibration factor.

According to one aspect of the invention, instead of contacting the cell and measuring current output, a capacitive sensor is held in close proximity to the cell, and senses the relative change in surface potential while the light is modulated. The change in surface potential, which is due to the collapse of the built in p-n junction potential under light-induced forward bias, acts as an indicator of the quantum efficiency. Thus, a relative quantum efficiency measurement can be performed without contacting the cell. The technique can be modified to use Kelvin probes or Monroe probes, in addition to the AC-coupled capacitive probe described here.

According to the invention, the sample temperature of either the entire sample or a localized portion of the sample is ramped while the QE is measured, so that QE can be plotted vs. sample temperature. In one aspect, the sample is on a conventional hot/cold temperature chuck. Further, the sample can be suspended or clamped onto an appropriate material, and heated with radiant energy from lamps. In another aspect, the sample is heated with a jet of hot air. Further, the sample may be heated by applying reverse bias current or forward bias current through the DUT, which warms up due to its internal resistance. In one aspect, the sample temperature is measured using conventional thermocouples or thermistors in contact with the cell or in contact with the chuck, which is in intimate thermal contact with the sample. In another aspect, the sample temperature is measured using non-contact microbolometers, thermopiles, InSb detectors, or other thermal imaging device. In one variation, the cell is moved from one test chuck to the next, and each chuck is held at a constant temperature. A QE measurement is performed above each test chuck, so that a curve of QE vs. temperature can be quickly assembled, using this multiple-station technique. The QE data may be plotted as a function of sample temperature, and a coefficient may be derived that describes the change in cell parameter vs. temperature.

In another aspect of the invention, the output from the conditioned light source, which includes the LED/filter assembly, can be modulated AC or adjusted, where a DC output can be part of the machine setup. In this case, the tilt of the interference filter may be modulated or adjusted to create a change in emitted wavelength. The DC adjustment capability may be used to 'push' LEDs to wavelengths that are most useful for a given type of solar cell. For instance, manufacturers of cells that use a CdS layer may wish to adjust several LED's so that they are crowded nearer to the CdS response peak.

The QE measurement head according to the current invention can also be used in combination with other similar QE heads. This may be useful to acquire QE data from several regions of a very large solar cell, or from front and back of a dual junction solar cell, etc. The heads may operate simultaneously if the chosen modulated frequency and phase to provide unique modulation signatures for each wavelength of light. As an alternative, the heads may be configured to use overlapping frequency space, but may be synchronized via a triggering scheme so that they sequentially measure the cell properties.

In one aspect of the invention, the QE measurement may be extended to a large number of measurement heads in order to provide a spatially resolved photoresponse of the cell. The number of wavelengths may also be reduced, as needed, to allow simplification of the device and to improve the spatial resolution.

For example, in the extreme case, a 2D array of LEDs such as an array of white LEDs, may be constructed. As described above, each LED may be modulated at a unique frequency. The 2D array of LED's is imaged using refractive optics, reflective optics, close proximity, or a combination thereof onto the sample surface, and the current output of the device is measured as a function of time. The FFT of the current or voltage output may be used to determine the photoresponse from each unique LED, and to plot a 2D map of cell photoresponse vs. position on the cell. This allows a full or partial wafer photoresponse map to be generated on the order of one second. The effective spatial resolution may be enhanced by moving the cell a fraction of the inter-LED spacing, and repeating the measurement, then deconvoluting the results using the known point-spread function of the LED's.

Figure 9:
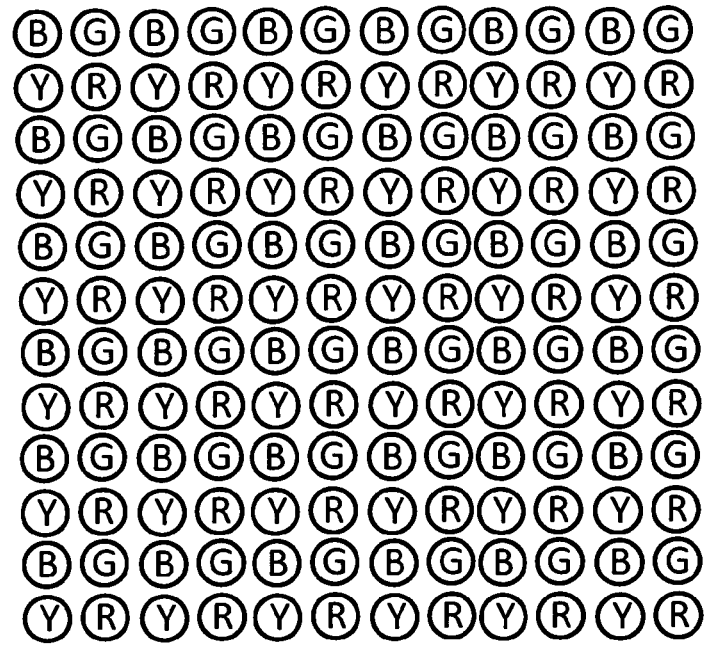
FIG. 9(a) shows a schematic of the LED locations with four colors arranged in a unit cell repeated to show a complete measurement grid according to the present invention.
FIG. 9(b) shows a schematic of the measurement locations according to the present invention.
FIG. 9(c) shows a schematic of a sparse array of LED's separated by a distance P and measurements taken by moving the measurement a distance P/2 according to the present invention.
Figure 9:
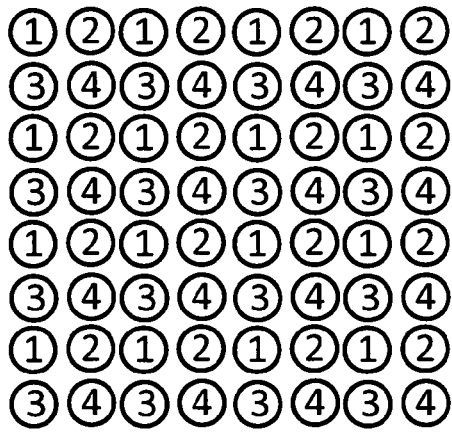
Figure 9:
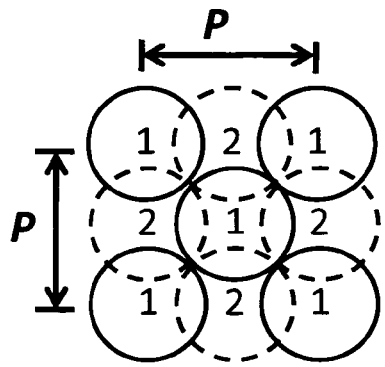

FIG. 9(a) shows a schematic of the LED locations with four colors (B, G, Y, R) arranged in a unit cell repeated to show a complete measurement grid 900. The "native" grid is 6×6 in this example. Larger native grids, resulting in larger complete grids, could be used and larger unit cells can include more than four colors. Rectangular grids and hexagonal arrangements are desirable, but other patterns would still work.

An example is provided here, where a 1D array of LEDs may be imaged onto the cell. The 1D array of light sources may be rastered across the cell by moving the cell, the optics, or a beamsteering mirror. Data acquisition is synchronized with beam rastering so that a 2D map of cell photoresponse vs. position can be reconstructed.

In the examples described above, spatial resolution may be traded for spectral resolution. For instance, in the 1D example red and blue LEDs may be arranged in alternating sequence: red/blue/red/blue/ . . . . Quantum efficiency is now measured at two wavelengths, with spatial resolution equal to the spacing between red LEDs. This concept may be extended to 2D by close-packing a unit cell of 2, 4, 9, etc. LED's, to give 2, 4, 9 . . . unique colors in a repeating spatial pattern. This allows the machine to extract conventional wavelength-dependent QE while simultaneously extracting spatial photoresponse information with resolution equal to the size of the unit cell. In this case, the four represented distinct LED colors (B, G, Y, R) in FIG. 9(a). One implementation would be for the LEDs to be packed, as shown in FIG. 9(a), but then a gap left between the LEDs and the DUT, allowing for natural diffraction of the LED beams such that they are more overlapping such that the spatial resolution approaches a 'unit cell' size, where the unit cell is the four LED's BGYR.

FIG. 9(b) shows a schematic of the measurement locations, for example four locations. A set of measurements is first performed at all locations 1 by a set of lightsources arranged on a regular pitch, P, then a small move (either of the optics or the sample, typically of distance P/N, is made before a second set of measurements is acquired at all positions 2. This process continues for positions 1 through N, where in this example N=4. The result is that N sets of spatially resolved measurements are acquired in sequence to provide QE data with spatial resolution P/N. In this example, the LED's are spaced on a pitch P that is larger than the distance between measurement sites. For example, one might use only white LEDs, located with a spacing equal to twice the diameter of the LED package, in both dimensions. With close proximity between the LED array and the DUT, only 25% of the DUT would be illuminated at any given time. A full measurement is made at positions 1, then either the DUT or the source is moved to illuminate positions 2 for a second measurement, then either the DUT or the source is moved to illuminate positions 3 for a third measurement, and so on . . . . This allows for a measurement resolution to exceed the number of LEDs, via temporal multiplexing FIG. 9(c) shows a schematic of a sparse array of LED's separated by a distance P and measurements taken by moving the measurement a distance P/2. Here, the solid-lined circle represents the initial position of the LED for a first measurement and the dashed-lined circle represents the second position for a second measurement. The figure shows the translation can be done horizontally or vertically alone, or horizontally and vertically together, where full coverage measurements are accomplished at P/2 resolution.

Figure 10:
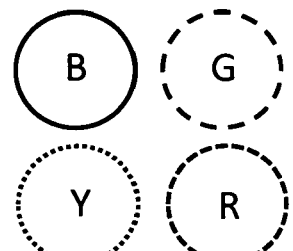
FIGS. 10(a)-(c) show a natural diffraction of the LED beams such that they are more overlapping according to the present invention.
Figure 10:
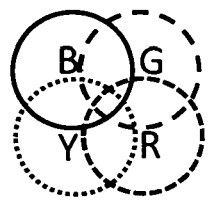
Figure 10:
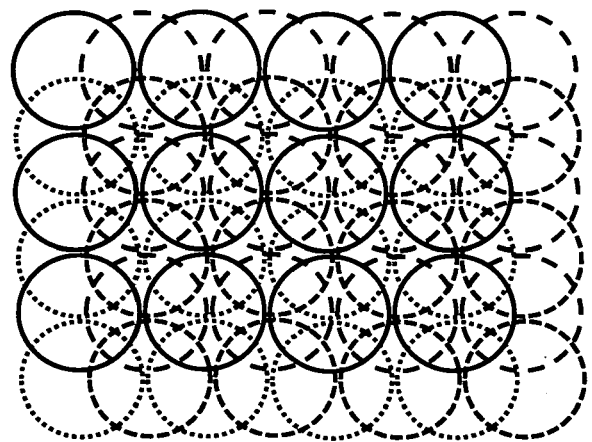

FIGS. 10(a)-10(c) show a natural diffraction of the LED beams such that they are more overlapping 1000. Accordingly, the cell is rastered or placed under the measurement head, continuous electrical contact may be made to the cell via brushes, roller contacts, or via the noncontact capacitive sensing described earlier. In one aspect of the invention, a polished bundle face could also be held in close proximity to the DUT, rather than imaging it onto the DUT with more optics.

According to the current invention, the apparatus described can be used to measure external QE, reflectance, and transmittance, where and by combining these three results, allows the determination of an internal quantum efficiency $QE_{int}=QE_{ext}/(1-R-T)$).

In one aspect, the current invention can be used for modulated reflectivity measurements, for example solar-modulated reflectivity is a technique that can be used to monitor the bandgap of a deposited material just after deposition, where often no contact is required to perform the measurement.

In a further aspect, the apparatus of the current invention may be used in combination with appropriate 'pump' beams to perform other measurements that can include photoreflectance and phototransmittance, where pump is defined as a bright light or laser. Other measurements include piezoreflectance and piezotransmittance, where pump is defined as power injected into the device via a piezo transducer, and further measurements include thermoreflectance and thermotransmittance, where pump is defined as heat injected via laser or IR source or conventional heater.

The QE measurement according to the current invention may be used to study time resolved changes in cell properties, due to its high measurement speed. For example amorphous silicon cells degrade under exposure to white light. The rate and magnitude of performance decay may be measured during a light soak. Plotting QE (at each wavelength) may be used to study the actual degradation mechanisms, where strong degradation in blue response indicates the degradation is near the cell surface, etc. In another example, organic solar cells often exhibit degradation soon after manufacture, sometimes within seconds or minutes. The high-speed QE device of the current invention may be used to measure initial performance, as well as the degradation vs. time, to quantify the degradation mechanisms.

The QE measurement according to the current invention may be used to perform combinatorial experiments, due to its high measurement speed. For example, a single solar cell may be prepared with a large number of unique surface passivation treatments arranged in known locations across the cell. The QE may be measured by the current invention at each of these sites, then the unique results may be compared to select the best surface passivation treatment. This may be extended to other treatments such as etches, ARC depositions, laser annealing, etc., which all benefit by conserving the number of cells needed for the experiment. In addition, measurements may be made before and after each treatment to better reject any cross-wafer variation in cell performance. This type of differential measurement can also be used when the cell is measured many times during a series of treatments, to extract the individual effects of each treatment.

In a further example the QE measurement device of the current invention may be used to sort cells into 'spectral bins'. For example, in a set of cells produce identical current output under standard white-light (AM1.5) test conditions where half of the cells have strong blue light response but lower red response, and half of the cells have low blue response but strong red response. The total factory output (in kW-hr) will be maximized if cells with similar spectral response are grouped together into modules during the build process. Without this binning, the total output of the module will be limited to the weakest performing cell. For instance, near sunrise and sunset the solar spectrum has weak blue output, so the module performance would be limited at these times by cells that have weak red response.

In a further aspect, the reflectance curve measured during the QE measurement may be used to sort cells according to color. This allows manufacturers to group cells that look alike into modules, to improve the look and visual uniformity of the product. Further, the QE measurement device of the current invention may be used to monitor the bandgap of the cell. This information may be passed back to the appropriate deposition chamber to adjust the parameters that control the bandgap, such as gas flows in an MOCVD reactor, deposition temperature of amorphous silicon, the mixture of a liquid precursor deposition system, individual layer thicknesses, etc.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art.

All such variations are considered to be within the scope and spirit of the present invention as defined by the following claims and their legal equivalents.

What is claimed:

1. A high-speed Quantum Efficiency (QE) measurement device comprising:
   a. at least one device under test (DUT);
   b. at least one conditioned light source, wherein said conditioned light source comprises at least one filtered LED having a less than 50 nm bandwidth, wherein a portion of said conditioned light source is monitored by light source monitoring elements comprising at least one collection optic and at least one photo detector;
   c. delivery optics, wherein said delivery optics direct said conditioned light source to said DUT;
   d. a controller, wherein said controller drives said conditioned light source in a time dependent operation, wherein a response by each said DUT from each said conditioned light source is uniquely identified;
   e. at least one reflectance measurement assembly, wherein said reflectance measurement assembly comprises at least one reflectance collection optic and at least one photo detector disposed to receive a portion of said conditioned light that is reflected from said DUT;
   f. a time-resolved measurement device comprising i) a current measurement device, ii) a voltage measurement device, or i) and ii), wherein said time-resolved measurement device is disposed to resolve i) a current, ii) a voltage or i) and ii) generated in said DUT by each said conditioned light source; and
   g. a sufficiently programmed computer disposed to determine and output an internal QE value for each said DUT according to an incident intensity of at least one wavelength of from said conditioned light source and said time-resolved measurement.

2. The high-speed QE measurement device of claim 1, wherein said conditioned light source comprises at least one conditioning optic disposed to reduce a bandwidth of said light source.

3. The high-speed QE measurement device of claim 1, wherein said determined internal QE value from said sufficiently programmed computer comprises parameters selected from the group consisting of a charge on an electron, said reflected light from said DUT, a number of photons per unit time of said conditioned light source directed at said DUT, measured transmitted light from said DUT, measured transmitted and reflected light from said DUT, a voltage generated by said DUT when illuminated by said conditioned light source, and an electric current generated by said DUT when illuminated by said conditioned light source.

4. The high-speed QE measurement device of claim 3, wherein said output internal QE value comprises a dimensionless quantity in a range of 0 to 1.

5. The high-speed QE measurement device of claim 1 further comprises a transmission detection assembly comprising at least one transmission photo diode, wherein said transmission detection assembly is disposed to measure a fraction of incident said conditioned light source transmitted through said DUT.

6. The high-speed QE measurement device of claim 1, wherein said time-dependent operation comprises pulsed operation or modulated operation.

7. A high-speed Quantum Efficiency (QE) measurement device comprising:
   a. at least one device under test (DUT);
   b. a controller;
   c. at least one conditioned light source comprising said controller driving each said conditioned light source in a pulsed operation, wherein a response by each said DUT from each said conditioned light source is uniquely identified;
   d. delivery optics, wherein said delivery optics direct said conditioned light source to said DUT;
   e. a time-resolved measurement device comprising i) a current measurement device, ii) a voltage measurement device, or i) and ii), wherein said time-resolved measurement device is disposed to resolve i) a current, ii) a voltage or i) and ii) generated in said DUT by each said conditioned light source; and
   f. a sufficiently programmed computer disposed to determine and output a QE value for each said DUT according to an incident intensity of at least one wavelength of from said conditioned light source and said time-resolved measurement.

8. The high-speed QE measurement device of claim 7, wherein a first said at least one conditioned light source is pulsed at a first pulse duration and another said at least one conditioned light source is pulsed at another pulse duration.

9. The high-speed QE measurement device of claim 7, wherein said conditioned light source comprises at least one conditioned LED having an output bandwidth less than 50 nm.

10. The high-speed QE measurement device of claim 7 further comprises an internal calibration sensor, where said internal calibration sensor comprises a sensor disposed to measure an intensity of said conditioned light source.

11. The high-speed QE measurement device of claim 10, wherein said internal calibration sensor comprises at least one sampling optic and at least one sampling photodiode.

12. The high-speed QE measurement device of claim 7, wherein said determined QE value from said sufficiently programmed computer comprises parameters selected from the group consisting of a charge on an electron, said reflected light from said DUT, a number of photons per unit time of said conditioned light source directed at said DUT, measured transmitted light from said DUT, measured transmitted and reflected light from said DUT, a voltage generated by said DUT when illuminated by said conditioned light source, and an electric current generated by said DUT when illuminated by said conditioned light source.

13. The high-speed QE measurement device of claim 12, wherein said output QE value comprises a dimensionless quantity in a range of 0 to 1.

14. The high-speed QE measurement device of claim 7 further comprises a transmission detection assembly comprising at least one transmission photo diode, wherein said transmission detection assembly is disposed to measure a fraction of incident said conditioned light source transmitted through said DUT.

15. The high-speed QE measurement device of claim 7 further comprises a reflection detection assembly comprising at least one reflection photo diode, wherein said reflection detection assembly is disposed to measure a fraction of incident said conditioned light source reflected from said DUT.

16. The high-speed QE measurement device of claim 7, wherein a unique duration of said pulse is assigned to each said conditioned light source, wherein a signal to noise ratio of the DUT response to each said conditioned light source is normalized to the DUT response caused by other said wavelengths.

17. The high-speed QE measurement device of claim 7, wherein a unique duration of said pulse is assigned to each unique said conditioned light source, wherein said assigned pulses normalize a time-averaged intensity of one said conditioned light source to another said conditioned light source over a light spectrum useful to said DUT.

18. The high-speed QE measurement device of claim 7, wherein a unique duration of said pulse is assigned to each wavelength from each said conditioned light source, wherein said assigned unique pulse is disposed to optimize a signal to noise ratio or the DUT response to said conditioned light source at a desired wavelength.

* * * * *